United States Patent [19]

Solinas et al.

[11] Patent Number: 5,560,899
[45] Date of Patent: Oct. 1, 1996

[54] PROCESS FOR SEPARATING HF FROM ITS MIXTURES WITH HYDROCHLOROFLUOROCARBONS 123 AND/OR 124

[75] Inventors: Giampaolo Solinas, Castellanza; Giampiero Basile, Alessandria, both of Italy

[73] Assignee: Ausimont S.p.A., Milan, Italy

[21] Appl. No.: 604,090

[22] Filed: Feb. 20, 1996

Related U.S. Application Data

[63] Continuation of Ser. No. 163,837, Dec. 7, 1993, abandoned.

[30] Foreign Application Priority Data

Dec. 10, 1992 [IT] Italy ............................... MI92A2799

[51] Int. Cl.$^6$ ....................................... C01B 7/19
[52] U.S. Cl. .................... 423/484; 423/488; 203/67; 203/88; 570/180; 570/177
[58] Field of Search .................... 423/484, 488; 203/71, 88, 67; 570/180, 177

[56] References Cited

U.S. PATENT DOCUMENTS

| | | | |
|---|---|---|---|
| 3,406,099 | 10/1968 | Buckman et al. | 203/50 |
| 3,947,558 | 3/1976 | van Eijl | 423/483 |
| 4,209,470 | 6/1980 | Lorquet | 280/652 |
| 4,382,895 | 5/1983 | Cole et al. | 562/33 |
| 4,465,842 | 8/1984 | Desbois et al. | 548/473 |
| 4,911,792 | 3/1990 | Manzer et al. | 203/39 |
| 4,944,846 | 7/1990 | Manzer et al. | 203/1 |
| 4,967,023 | 10/1990 | Carmello et al. | 570/166 |
| 5,100,639 | 3/1992 | Freire et al. | 423/484 |
| 5,200,431 | 4/1993 | Dattani et al. | 570/178 |

FOREIGN PATENT DOCUMENTS

| | | |
|---|---|---|
| 0003147 | 7/1979 | European Pat. Off. |
| 0353970 | 2/1990 | European Pat. Off. |
| 718682 | 11/1954 | United Kingdom |

OTHER PUBLICATIONS

Hawley, Gessner The Condensed Chemical Dictionary, 10 ed. 1981, p. 465 (no month).
European Search Report dated Mar. 15, 1994 for EP 93 11 8728.

*Primary Examiner*—Ngoc-Yen Nguyen
*Attorney, Agent, or Firm*—Bryan Cave LLP

[57] ABSTRACT

The invention relates to a process for separating HF contained in liquid mixtures comprising HCFC 123 and/or 124. The mixtures, enriched in $C_2Cl_4$ up to a content of such compound of 20–75% by weight, is subjected to a treatment for separating liquid phases, thereby obtaining an acid phase very rich in Hf and an organic phase impoverished in HF, which is subjected to a flash, so obtaining a liquid phase containing 123, 124 and $C_2Cl_4$, having a very low HF content, and a gas phase enriched in HF. As an alternative to flash, a separation in a distillation column can be carried out.

5 Claims, No Drawings

PROCESS FOR SEPARATING HF FROM ITS MIXTURES WITH HYDROCHLOROFLUOROCARBONS 123 AND/OR 124

This is a continuation of U.S. application Ser. No. 08/163,837, filed Dec. 7, 1993 now abandoned.

BACKGROUND OF THE INVENTION

The present invention relates to a process for separation of hydrofluoric acid from is mixtures with 1,1,1-trifluoro-2,2-dichloroethane (HCFC 123) and/or 1,1,1,2-tetrafluoro-2-chloroethane (HCFC 124) and other halocarbon compounds, if any.

Various methods of separating and recovery HF from fluorocarbon composition are described in the art.

According to U.S. Pat. No. 3,406,099, the separation of $CF_3COCF_3$, HF and $CFCl_2 CClF_2$ from their mixtures is carried out via azeotropic distillation.

U.S. Pat. No. 3,947,558 describes a process for separating HF from the fluorination products of chlorocarbons having 1–3 carbon atoms, which comprises the initial step of separating HCl, if any, then cooling the mixture in order to obtain two liquid phases, one rich in HF and the other poor in HF, and treating the latter with a glycol having 2–8 carbon atoms, so obtaining a glycolic phase rich in HF, which is then recovered by distillation.

According to U.S. Pat. No. 4,209,470, HF is separated from its liquid mixtures with 1-chloro-1,1-difluoroethane by addition of an auxiliary solvent selected from 1,1-dichloro-1-fluoroethane, vinylidene chloride and 1,1,1-trichloroethane with separation of a liquid phase impoverished in HF, from which HF is then separated by distillation.

Lastly, according to U.S. Pat. No. 4,944,846, the separation of HF from its mixtures with HCFC 123 and/or 124 is obtained by regulating the HF/HCFC 123 molar ratio in such mixture to values not exceeding 1.3, and then by subjecting said mixture to azeotropic distillation, thereby obtaining a head portion containing substantially all the HF and a part of HCFC 123 in the form of a HF/HCFC 123 azeotrope and, maybe, a HF/HCFC 124 azeotrope and a tail portion substantially free from HF, containing HCFC 123.

SUMMARY OF THE INVENTION

The Applicant has now found a process for separating HF from its mixtures comprising HCFC 123 and/or HCFC 124 which does not require azeotropic distillations.

In fact, the Applicant has surprisingly found that it is possible to obtain a separation of the HF contained, even in small concentrations, in liquid mixtures comprising HCFC 123 and/or HCFC 124, if a $C_2Cl_4$ amount ranging from 20 to 75% by weight calculated on the total of the mixtures, is added to such mixtures and if they are subjected to a treatment for separating two liquid phases, under particular conditions, so obtaining an organic phase poor in HF, which is subjected to a partial vaporization by flash according to particular modalities.

From the flash treatment, a head portion (vapour phase) enriched in HF, comprising HCFC 124 and HCFC 123 and small amounts of $C_2Cl_4$, and a tail portion (liquid phase), substantially free from HF and containing HCFC 123, HCFC 124 and $C_2Cl_4$ are obtained.

Thus, it is an object of the present invention to provide a new process for separating HF from its mixtures containing HCFC 123 and/or HCFC 124.

Another object is to provide a process, simplified with respect to those of the prior art, which allows in particular, when so desired, the use of distillation columns to be avoided.

These and still other objects are achieved by the process of the present invention for separating HF contained in liquid mixtures comprising hydrochlorofluorocarbons 123 and/or 124.

DETAILED DESCRIPTION OF THE INVENTION

This process is characterized in that:

1) to such mixtures, tetrachloroethylene is added in such amounts that the proportion by weight of tetrachloroethylene ranges from 20 to 75% by weight in the resulting mixtures, such operation not being required if the mixtures to be treated comprising HF, 123 and/or 124 already exhibit a tetrachloroethylene content in the above indicated range;

2) maintaining the mixtures coming from the first step at a temperature selected in the range of from −40° C. to +50° C. and a pressure equal to or higher than the total vapour tension of the mixtures at the above said temperature, obtaining two liquid phases, which are separated, the lighter one having a very high HF content and the denser one being an organic phase impoverished in HF;

3) the organic phase is subjected to a partial vaporization treatment by means of flash, operating so as to obtain a vaporization of 15–60% by weight of the inflowing organic phase, under a pressure ranging from 0.1 to 2 Mpa abs.;

4) after having substantially reached the equilibrium between the gas phase and the liquid phase, the liquid phase, substantially free from HF and containing HCFC 123, HCFC 124 and tetrachloroethylene, is separated from the gas phase enriched in HF and containing HCFC 123, HCFC 124 and tetrachloroethylene.

According to an alternative to such process, after having carried our steps 1) and 2) described hereinbefore, the organic phase is subjected to separation in a distillation column, according to the art.

The partial vaporization by means of flash—usually referred to as "flash" by the technicians—is, as is known, an operation in which a liquid mixture is partially vaporized in an apparatus having appropriate dimensions, in which the two phases (gaseous and liquid) are maintained in contact until the equilibrium between them is substantially reached, then they are separated and removed from the apparatus.

The step in which the two liquid phases are formed and separated, according to the present invention, can be effected either continuously of discontinuously.

The separation is carried out by means of known techniques such as gravity deposition, centrifugation and flow through porous membranes.

In said step for the formation and separation of the two liquid phases, it is preferably operated at temperatures ranging from 0° to 30° C. and at pressures preferably ranging from 0.1 to 1 Mpa abs. The liquid acid phase can be conveniently recycled to the HCFC synthesis reactor.

In the flash operation, which can be conducted continuously of discontinuously, preferably a pressure ranging from 0.5 to 1.0 Mpa abs is operated. Preferably, such operation is conducted so as to vaporize from 20 to 50% by weight of the inflowing organic phase.

The vapour phase is preferably recycled at a point in the plant between the HCFC synthesis and the separation of the liquid phases.

The liquid phase obtained at the end of flash has such a low residual HF content that in several cases it is not necessary to remove the residual HF because, for example, it will be at any rate eliminated during the purification operations of the HCFC to be obtained.

However, if so desired, the residual HF of the liquid phase can be removed by means of conventional techniques: for example, it is possible to vaporize the liquid phase and to treat it with an alkaline aqueous solution, whereafter the organic components can be separated from one another by distillation.

While the HF-containing mixture, which is treated according to the present invention, can come from various sources, an advantageous embodiment of the present invention resides in treating the mixture flowing from the preparation of HCFC 123 and/or 124 by reaction of tetrachloroethylene with HF, for example conforming to the process of U.S. Pat. No. 4,967,023.

The mixture coming from such reaction usually comprises HF, HCFC 123 and 124, tetrachloroethylene, HCl and minor amounts of halogenated compounds such as 1,2,2-trichloro-1,1-difluoroethane (HCFC 122) and perfluoroethane (HFC 125).

In this case, the mixture to be treated is preferably deprived in advance of HCl and HFC 125 contained in it by means of conventional techniques, for example by distillation or rectification.

Of course, if the mixtures obtained from such reaction contain amounts of tetrachloroethylene lower than 20% by weight, it will be necessary to secure that the content of such composition in the mixture is in the required range of from 20 to 75% by weight, as indicated hereinbefore, by effecting suitable additions of said compound to the mixture to be treated.

The following examples are given merely for the purpose of illustration and are not intended to limit the scope of the invention. In said examples, the pressures are indicated in absolute values.

All the compositions of the mixtures have been determined by gas chromatography for the organic components and by acidimetric titration with regard to HF. Each analysis has been carried out 4 times, and the compositions reported in the Tables indicate the average values determined in such analyses.

Also in the flash operation, the vaporization degree of the inflowing organic phase is indicated as average value.

EXAMPLE 1

A gaseous phase coming from a synthesis process of 123 and 124 by hydrofluorination reaction of $C_2Cl_4$ was condensed at 25° C. $C_2Cl_4$ was added to the liquid phase until composition A reported in Table 1 was obtained. The liquid phase enriched in $C_2Cl_4$ was treated in a liquid phase separator of about 2 litre volume, where a pressure of 0.3 MPa was dominant.

From the separator, an upper phase essentially consisting of HF and a lower organic phase of composition B (see Table 1) were drawn. From the organic phase having composition B, a sample of 141.2 g was taken, which was subjected to flash in a pressure vessel of 1.060 litre volume.

The pressure in the vessel was 0.5 MPa and the temperature was 60.3° C. Once the equilibrium between vapour phase and liquid phase had been reached, which was apparent from the constant temperature and pressure (the operation was conducted, for operative convenience, over 14 hours), the vapour phase percentage was of 34% by weight. Then, the two phases were separated.

The gaseous phase had composition C reported in Table 1, while the liquid phase had composition D, also reported in Table 2.

TABLE 1

| Components | Composition A: fed to the liquid phase formation and separation step (% by weight) | Composition B: liquid organic phase obtained after liquid phase separation (% by weight) | Composition C: vapor phase obtained by means of flash (% by weight) | Composition D: liquid phase obtained by means of flash (% by weight) |
| --- | --- | --- | --- | --- |
| $C_2Cl_4$ | 29.4 | 29.8 | 1.2 | 36.4 |
| HCFC 123 | 34.2 | 34.6 | 26.5 | 37.9 |
| HCFC 124 | 34.4 | 34.8 | 71.1 | 25.6 |
| HF | 2.0 | 0.8 | 1.2 | 0.09 |

EXAMPLE 2

Starting from a different mixture enriched in $C_2Cl_4$, the general procedure of example 1 was followed, except that:

the amount of organic phase fed to flash was of 139.5 g;

in the flash vessel, the temperature was of 79.3° C.

The vaporization degree was 27% by weight.

The compositions of the various phases are reported in Table 2.

TABLE 2

| Components | Composition A: fed to the liquid phase formation and separation step (% by weight) | Composition B: liquid organic phase obtained after liquid phase separation (% by weight) | Composition C: vapor phase obtained by means of flash (% by weight) | Composition D: liquid phase obtained by means of flash (% by weight) |
|---|---|---|---|---|
| $C_2Cl_4$ | 49.0 | 49.9 | 5.57 | 63.0 |
| HCFC 123 | 29.5 | 29.9 | 38.0 | 24.05 |
| HCFC 124 | 19.5 | 19.9 | 55.3 | 12.9 |
| HF | 2.0 | 0.3 | 0.95 | 0.045 |

EXAMPLE 3

Starting from another mixture enriched in $C_2Cl_4$, the general procedure of example 1 was followed, except that:

the amount of organic phase fed to flash was of 152.1 g;

in the flash vessel, the temperature was 108.5° C.

The vaporization degree was equal to 27% by weight.

The compositions of the various phases are reported in Table 3.

TABLE 3

| Components | Composition A: fed to the liquid phase formation and separation step (% by weight) | Composition B: liquid organic phase obtained after liquid phase separation (% by weight) | Composition C: vapor phase obtained by means of flash (% by weight) | Composition D: liquid phase obtained by means of flash (% by weight) |
|---|---|---|---|---|
| $C_2Cl_4$ | 68.5 | 70.0 | 18.7 | 84.2 |
| HCFC 123 | 19.6 | 19.9 | 34.8 | 13.0 |
| HCFC 124 | 9.8 | 10.0 | 45.6 | 2.8 |
| HF | 2.1 | 0.12 | 0.90 | 0.02 |

EXAMPLE 4

This example illustrates a flash operation.

A liquid mixture (614 g) of composition B was subjected to a flash operation according to the general modalities of example 1, with the exception that in the flash vessel, which had a volume of 610 ml, the pressure was of 0.66 MPa and the temperature of 78.6° C.

The compositions of vapour phase C and liquid phase D obtained by means of flash are reported in Table 4.

TABLE 4

| Components | Composition B: liquid organic phase subjected to flash (% by weight) | Composition C: vapor phase obtained by means of flash (% by weight) | Composition D: liquid phase obtained by means of flash (% by weight) |
|---|---|---|---|
| $C_2Cl_4$ | 39.93 | 1.713 | 40.23 |
| HCFC 123 | 39.93 | 33.287 | 39.98 |
| HCFC 124 | 20.05 | 64.25 | 19.70 |
| HF | 0.094 | 0.75 | 0.090 |

We claim:

1. A process for the separation of hydrogen fluoride from a liquid mixture comprising hydrogen fluoride and a chlorofluorohydrocarbon liquid selected from the group consisting of 1,1,1-trifluoro-2,2-dichloroethane, 1,1,1,2-tetrafluoro-2-chloroethane, and mixtures thereof, the process comprising:

(a) adding tetrachloroethylene to the liquid mixture in an amount such that the resulting mixture contains from 20% to 75% by weight of tetrachloroethylene;

(b) subjecting the mixture from step (a) to a temperature of from −40° to +50° C., and to a pressure at least equal to the total vapor tension of the mixture from step (a) at said temperature, so that two liquid phases are formed, a light phase, and a dense organic phase;

(c) separating the two liquid phases;

(d) subjecting the dense organic phase to a partial flash vaporization operation to vaporize 15% to 60% by weight of the dense organic phase, under an absolute pressure of 0.1 to 2 MPa, resulting in two phases, a substantially hydrogen fluoride-free liquid phase comprising tetrachloroethylene and the chlorofluorohydrocarbon liquid and a hydrogen fluoride-enriched gaseous phase;

(e) separating the resulting substantially hydrogen fluoride-free liquid phase from the hydrogen fluoride-enriched gaseous phase.

2. The process of claim 1, wherein the temperature during formation and separation of the two liquid phases is from 0° to 30° C.

3. The process of claim 1, wherein the absolute pressure during formation and separation of the two liquid phases is from 0.1 to 1 MPa.

4. The process of claim 3, wherein the absolute pressure during the partial flash vaporization operation is from 0.5 to 1.0 MPa.

5. The process of claim 1 wherein the partial flash vaporization operation vaporizes from 20% to 50% by weight of the dense organic phase.

* * * * *